United States Patent
Selim

(10) Patent No.: US 6,544,557 B2
(45) Date of Patent: Apr. 8, 2003

(54) EFFERVESCENT TABLET COMPOSITIONS

(75) Inventor: James Selim, Moorebank (AU)

(73) Assignee: Pan Pharmaceutical Limited, Moorebank (AU)

( * ) Notice: Subject to any disclaimer, the term of this patent is extended or adjusted under 35 U.S.C. 154(b) by 0 days.

(21) Appl. No.: 09/940,692

(22) Filed: Aug. 27, 2001

(65) Prior Publication Data

US 2002/0127184 A1 Sep. 12, 2002

Related U.S. Application Data

(60) Provisional application No. 60/260,418, filed on Jan. 9, 2001.

(51) Int. Cl.⁷ .............................. A61K 9/32; A61K 9/46
(52) U.S. Cl. ....................................... 424/482; 424/466
(58) Field of Search ................... 424/482, 466

(56) References Cited

U.S. PATENT DOCUMENTS

| | | | |
|---|---|---|---|
| 3,789,119 A | | 1/1974 | Fusari et al. |
| 3,873,727 A | | 3/1975 | Fusari et al. |
| 4,036,228 A | * | 7/1977 | Theeuwes .................... 128/260 |
| 4,704,119 A | | 11/1987 | Shaw et al. |
| 4,885,173 A | | 12/1989 | Stanely et al. |
| 5,004,614 A | * | 4/1991 | Staniforth .................... 424/466 |
| 5,437,872 A | | 8/1995 | Lee |
| 5,466,464 A | | 11/1995 | Masaki et al. |
| 5,484,602 A | | 1/1996 | Stanely et al. |
| 5,576,014 A | | 11/1996 | Mizumoto et al. |
| 5,807,577 A | | 9/1998 | Ouali |
| 5,869,095 A | | 2/1999 | Gergely et al. |
| 5,895,664 A | | 4/1999 | Cherukuri et al. |
| 5,912,012 A | | 6/1999 | Carlin et al. |
| 6,083,531 A | | 7/2000 | Humbert-Droz et al. |
| 6,106,861 A | | 8/2000 | Chauveau et al. |
| 6,110,927 A | | 8/2000 | Buckland et al. |

* cited by examiner

Primary Examiner—Theodore J. Criares
Assistant Examiner—Jennifer Kim
(74) Attorney, Agent, or Firm—Ray K. Shahani, Esq.

(57) ABSTRACT

An effervescent sub-lingual type composition, optionally in tablet form, comprising at least one active ingredient, one ore more fruit acids, and one or more effervescing alkalis, wherein at least the acid component(s) have been coated with protective layer of polydimethylsiloxane that substantially minimizes contact between the acid(s) and atmospheric moisture until the composition is purposely mixed with water or is used sub-lingually. A method of preparation of the effervescent compositions is also dislcosed.

3 Claims, No Drawings

EFFERVESCENT TABLET COMPOSITIONS

PRIORITY CLAIM AND RELATED APPLICATIONS

This application is related to, claims benefit of priority of filing under, and incorporates herein by reference in its entirety, Australian Provisional Application No. PQ9722 filed Aug. 28, 2000 entitled EFFERVESCENT TABLET COMPOSITIONS, and U.S. Provisional Application Serial No. 60/260,418 filed Jan. 9, 2001, and claims any and all benefits to which it is entitled therefrom.

FIELD OF THE INVENTION

The present invention relates to improvements in tablet manufacture and to tablets manufactured by the process of this invention.

More specifically, the invention relates to an improved tablet formulation that permits the manufacture of effervescent sub-lingual type tablets in a normal or ambient environment and at the same time resulting in tablets that are less affected by atmospheric humidity. The invention also relates to a method or process for manufacturing such products.

The present invention permits the manufacture of effervescent sub-lingual type tablets that are designed to be placed under the tongue and sucked until completely dissolved. This technique of administration is similar to conventional sub-lingual tablets which allow for fast absorption of the pharmaceutically or therapeutically active ingredients from the stomach.

BACKGROUND

The value of sub-lingual tablets has been recognized for many years as a very effective dosage form that permits the active ingredient(s) to be quickly utilized by the body.

This is of particular value where rapid availability of the active ingredients is desired. For example glyceryl trinitrate sub-lingual tablets are prescribed for patients suffering from the acute anginal pain, in the long term management of angina pectoris and in cardiac emergencies. An essential pre-requisite is that the active ingredient must be rapidly released while in the mouth, otherwise the needed quick relief is not achieved.

However, a common feature of sub-lingual tablets is poor palatability. Because of the effervescent base, and the inclusion of flavours, the novel formulae of the present invention not only assures dissolution of the tablets in saliva by releasing the active ingredients as a microsuspension that facilitates prompt absorption but also provides a pleasant taste which reduces any patient resistance.

This feature is of particular value with products formulated for children.

Effervescence is achieved by including an acid, for example, citric acid and/or tartaric acid, and an effervescing alkali, for example sodium bicarbonate, potassium bicarbonate and/or calcium carbonate, in the formula. In the presence of traces of water, these ingredients react, forming bubbles of carbon dioxide and liberating more water that further promotes the reaction. Depending on the nature of the active ingredient(s), which may be either soluble in water or are converted to the sodium salt(s) which are then dissolved, all ingredients of effervescent sub-lingual tablets are typically dissolved before ingestion.

Generally, the amount of moisture in the atmosphere is sufficient to start this reaction, so a very low relative humidity, typically less than 10%, in the environment is required for all processing and packaging stages. Further, it has often been necessary to individually wrap each tablet to protect it from moisture during packaging and distribution.

OBJECTS AND ADVANTAGES OF THE INVENTION

It is an object and an advantage of the present invention to provide an effervescent sub-lingual type tablet and a method or process of manufacturing same which goes at least some way towards overcoming or at least minimizing the prior art problems or limitations outlined above, or for providing a clear alternative choice for customers.

It is another object and advantage of this invention to provide an effervescent sub-lingual tablet and a method or process of manufacturing same which is relatively stable under normal or ambient conditions.

It is a further object and advantage of this invention to provide an effervescent sub-lingual type tablet formulation, where the manufacture thereof is possible in an environment wherein no special precautions (apart from mechanical ventilation) have been taken to minimize the relative humidity of the air during the processing and the packaging thereof.

It is yet another object and advantage of this invention to provide a sub-lingual type tablet formulation which does not require any special protection from atmospheric moisture during subsequent storage, or packaging and storage both before and after sale.

These and other objects of this invention will become more apparent from the following description.

SUMMARY OF THE INVENTION

According to one aspect of the invention there is provided an effervescent sub-lingual type composition, and especially a flavored effervescent tablet composition or formulation, which includes at least one active ingredient, one or more fruit acids, e.g., citric acid or tartaric acid and one or more effervescing alkalis, e.g., sodium bicarbonate, potassium bicarbonate and/or calcium carbonate, amongst the active ingredients of the composition, wherein the acid component(s) of the composition has been pre- or post-coated with a protective layer of a polydimethylsiloxane which substantially minimises contact between the acid and atmospheric moisture until the composition is purposely mixed with water.

According to another aspect of the invention there is provided a method of preparation of an effervescent composition, and especially an effervescent medicinal or therapeutic composition, wherein the acid(s) or other effervescing components are pre-coated with a polydimethylsiloxane before the coated component is further mixed with the other composition ingredients.

Preferably, the pH of the polydimethylsiloxane is similar to that of the acid component, typically pH 2–3. Preferably, the concentration of the polydimethylsiloxane varies in the range of about 0.05 to about 1.5% of the total weight of the composition.

DETAILED DESCRIPTION OF THE PREFERRED EMBODIMENT(S)

The pre-coating of the effervescent acid component(s) of the composition effectively precludes any reaction with the alkali component(s) because of the atmospheric moisture, even when the relative humidity of the air is more than about ten percent (10%).

Further, compressed tablets manufactured according to the invention do not require any special protection from atmospheric moisture during subsequent storage, packaging and storage both before and after sale.

Preferably, according to the invention, the acid is loaded into the mixing bowl of a granulating machine fitted with a two speed planetary mixing blade and separate horizontally mounted high speed chopper mixer. The polydimethylsiloxane is added and the conventional mixing blade is switched on, with high speed being selected. Mixing continues until all of the acid has been coated with this material and a damp, solid mass has been formed. After this has been achieved, the chopper-mixer of the machine is switched on and the mass is subjected to this treatment for about 0.5 to 1.0 minutes, followed by about a further 2–5 minutes of high speed mixing by the planetary blade.

The mixture is then discharged from the granulating machine onto stainless steel trays in thin layers. These trays are then loaded into a drying oven preheated to and set at 50 degrees Centigrade for about 18 hours to dry. It is then reloaded into the granulating machine.

According to one embodiment using citric acid and using a Karl Fischer Titrator apparatus, the maximum water content of the coated citric acid is 0.2% w/w.

The other ingredients in the formula including the effervescing alkali(s) are added to the granulating machine, which is then switched on, using the planetary mixing blade at high speed, for about 305 minutes. The dry mixture is then unloaded and compressed into tablets.

EXAMPLE(S)

The present invention will be further described and illustrated with reference to the following non-limiting example.

A typical sub-lingual type tablet formulation is described and includes co-enzyme Q10 (ubidecarenone), mannitol, xylitol sweeteners, lime and lemon flavours, and other ingredients.

| Ingredient | Weight (mg) |
| --- | --- |
| Citric Acid | 229 |
| Polydimethylsiloxane (special grade) | 3 |
| Sodium Bicarbonate | 187 |
| Xylitol (special grade) | 1 |
| Microcrystalline cellulose | 80 |
| Co-enzyme Q10 | 57.5 |
| Sucralose | 4 |
| Lime flavour powder | 6 |
| Lemon flavour powder | 6 |
| Silica colloidal | 16 |
| Magnesium Stearate | 5.5 |
| Individual Tablet Weight | 595 |
| Tablet Diameter 11.1 mm (14/32 inches) | |

Other active ingredients of other sub-lingual tablets include but are not limited to zinc gluconate, Echinacea, ascorbic acid and its salts, guarana, paracetamol, ibuprofen, ginger, diphenhydramine hydrochloride and multi-vitamin-mineral mixtures.

The formulae and processing procedures according to the present invention permit the manufacture, storage and packaging of effervescent sub-lingual type tablets in a manufacturing environment where the temperature but not the relative humidity of the air is controlled. As a result, the cost of both initial investment and operations in processing and packaging are significantly reduced. Still further savings in the costs of packaging are achievable because it is not necessary to individually wrap each such tablet for protection. The effervescent sub-lingual type tablets allow for fast absorption of the active ingredients from the stomach for immediate beneficial therapeutic effect.

Although exemplary embodiments of the present invention have been shown and described, it will be apparent to those having ordinary skill in the art that a number of changes, modifications or alterations to the invention described herein may be made, none of which depart from the spirit of the present invention. All such changes, modifications, and alterations should therefore be seen as being within the scope of the present invention.

It should be appreciated that the present invention provides a substantial advance in the manufacture and storage of effervescent sub-lingual type formulations, providing all of the herein-described advantages without incurring any relative disadvantages.

The terms "comprise", "comprises" and "comprising", as used herein, are used in the inclusive sense of "having", or "including", and not in the exclusive sense of "consisting only of".

I claim:

1. A method for preparing an effervescent composition in a manufacturing environment where the temperature but not the relative humidity of the air is controlled, the method comprising the following steps:
   1. Loading one or more fruit acids into a granulating machine;
   2. Adding polydimethylsiloxane to the granulating machine;
   3. Mixing the one or more fruit acids with the polydimethyisiloxane until all of the acid has been coated with polydimethylsiloxane;
   4. Adding one or more effervescing alkalis to the granulating machine; and
   5. Compressing the mixture into tablets.

2. The method of claim 1 in which the mixture of acid coated with polydimethylsiloxane is dried prior to adding the one or more effervescing alkalis to the granulating machine.

3. The method of claim 2 in which the mixture of acid coated with polydimethylsiloxane is dried to the point where the maximum water content of the coated citric acid is 0.2% w/w.

* * * * *